United States Patent [19]

Nowak et al.

[11] Patent Number: 4,463,198

[45] Date of Patent: Jul. 31, 1984

[54] METHOD FOR THE REARRANGEMENT OF DIALKYLBENZENE DIHYDROPEROXIDES TO DIHYDRIC PHENOLS

[75] Inventors: Edward N. Nowak, Akron; William S. Hollingshead, Cuyahoga Falls; Joel Muse, Jr., Kent, all of Ohio

[73] Assignee: The Goodyear Tire & Rubber Company, Akron, Ohio

[21] Appl. No.: 410,613

[22] Filed: Aug. 23, 1982

[51] Int. Cl.$^3$ ............................................. C07C 37/08
[52] U.S. Cl. .................................. 568/768; 568/741; 568/798
[58] Field of Search ..................... 568/768, 741, 798

[56] References Cited

U.S. PATENT DOCUMENTS

| 4,049,723 | 9/1977 | Tanaka et al. | |
|---|---|---|---|
| 4,112,244 | 9/1978 | Nowak et al. | 568/768 |
| 4,119,791 | 10/1978 | Hollingshead | 568/768 |
| 4,207,264 | 6/1980 | Anderson et al. | 568/768 |
| 4,229,596 | 10/1980 | Nowak et al. | |

Primary Examiner—Werren B. Lone
Attorney, Agent, or Firm—C. James Bushman; Alvin T. Rockhill

[57] ABSTRACT

An improved method for the acid-catalyzed rearrangement of a dialkylbenzene dihydroperoxide to a dihydric phenol which eliminates the formation of an emulsion during the subsequent separation and recovery of the dihydric phenol in a process which utilizes water, the method comprising the addition of the acid as a solution in a water soluble organic solvent, preferably a ketone, which is non-reactive with the acid.

7 Claims, No Drawings

METHOD FOR THE REARRANGEMENT OF DIALKYLBENZENE DIHYDROPEROXIDES TO DIHYDRIC PHENOLS

BACKGROUND OF THE INVENTION

This invention relates to an improved method for rearranging diisopropylbenzene dihydroperoxides to dihydric phenols such as hydroquinone and resorcinol whereby an emulsion is eliminated in the subsequent steps of separating and recovering the dihydric phenol from the complex reaction product.

It is known to oxidize dialkylbenzenes to the corresponding dialkylbenzene dihydroperoxide, and to rearrange the dihydroperoxide to the corresponding dihydric phenol. See for example Tanaka, et al U.S. Pat. No. 4,049,723, incorporated herein by reference for all purposes, the references disclosed therein, and the paper by J. Ewers, H. W. Voges and G. Maleck entitled "Process for the Production of Hydroquinone", Erdoel Kohle Erdgas, Petrochem. Br. Chem., Vol. 28, No. 1, 1975, pp. 34+. For example, the rearrangement of para-diisopropylbenzene dihydroperoxide to hydroquinone is accomplished by the acid-cleavage, in a ketone solvent such as methyl isobutyl ketone, of the para-diisopropylbenzene dihydroperoxide with an acid catalyst (Hoch splitting). Prior to rearrangement, the para-diisopropylbenzene dihydroperoxide is present in a complex mixture of by-products of the oxidation of the para-diisopropylbenzene. The hydroquinone must be subsequently recovered from such by-products and the ketone solvent present during the rearrangement.

As discussed in Tanaka, et al U.S. Pat. No. 4,049,723, various methods have been proposed for separating the hydroquinone from the by-products and ketone solvent. Invariably, in those processes wherein water is present, an emulsion is formed which makes the separation extremely difficult, time consuming and expensive. The process disclosed by Tanaka, et al eliminates the use of water during the separation step but has the disadvantage of adding large quantities of an aromatic hydrocarbon to the hydroquinone containing rearrangement product. The aromatic hydrocarbon must itself be subsequently recovered which presents further processing problems.

SUMMARY OF THE INVENTION

We have now found that the formation of an emulsion during the separation of a dihydric phenol such as hydroquinone or resorcinol from the complex mixture resulting from the acid-catalyzed rearrangement of the precursor diisopropylbenzene dihydroperoxide in a ketone solvent can be eliminated by adding a suitable water soluble organic solvent to the acid used in the rearrangement prior to the addition of the acid to the diisopropylbenzene dihydroperoxide containing mixture.

Thus in its broadest aspects, the invention comprises the addition of the acid in a process for the rearrangement of a dialkylbenzene dihydroperoxide to a dihydric phenol as a solution in a suitable water soluble organic solvent.

Accordingly, it is an object to provide an improved method of rearranging a dialkylbenzene dihydroperoxide to dihydric phenol which eliminates the formation of an emulsion in the subsequent steps of separating and recovering the dihydric phenol from the complex rearranged product.

It is another object of this invention to provide a method of eliminating the formation of an emulsion during the separation and recovery of a dihydric phenol obtained by acid-cleavage of an oxidation product of a diisopropylbenzene in a solvent such as a ketone.

It is still another object of this invention to provide an improved method for separating a dihydric phenol such as hydroquinone, in high yields, from a complex mixture obtained by acid-cleavage of an oxidation product of a diisopropylbenzene in a solvent.

These and other objects of this invention will become apparent to one skilled in the art upon reading the following description of the invention and the appended claims.

DESCRIPTION OF PREFERRED EMBODIMENTS

While the present invention will be described with particular reference to the rearrangement of para-diisopropylbenzene dihydroperoxide to produce hydroquinone, it is to be understood that it is equally applicable to the production of other dihydric phenols such as, for example, the production of resorcinol from m-diisopropylbenzene dihydroperoxide.

Methods for oxidizing dialkylbenzenes, such as meta and para-diisopropylbenzene, to meta and para-diisopropylbenzene dihydroperoxide are well known in the art, and the complex mixture containing the diisopropylbenzene dihydroperoxide, which is the starting material for the process of this invention, can be obtained by these known methods.

Moreover, methods for acid-cleaving the diisopropylbenzene dihydroperoxides in such complex mixtures to dihydric phenols with an acid catalyst in the presence of a ketone solvent are also well known. For example, an oxidation product of diisopropylbenzene is directly cleaved in the presence of an acid-containing catalyst, for example, sulfuric acid, perchloric acid, phosphoric acid, p-toluenesulfonic acid, or a cation-exchange resin in H+-form. Methyl isobutyl ketone (MIBK) is most suitable as the ketone solvent used for acid-cleavage. Aromatic hydrocarbons used in a step of distilling low-boiling fractions from the rearrangement product can be used as solvents together with the ketone solvent.

A satisfactory process for the continuous rearrangement of para-diisopropylbenzene dihydroperoxide is achieved by maintaining certain process conditions. Too high a water content leads to an extension of rearrangement time and to poorer yields of hydroquinone. Too high a sulfuric acid concentration or too high a temperature leads to a poorer yield of hydroquinone. Too low a sulfuric acid concentration or too low a temperature causes a lengthening of the rearrangement time. The solution added to the rearranger must have a minimal concentration of para-diisopropylbenzene dihydroperoxide of 6 to 7%, otherwise excessive rearrangement time and reduced yield occur. Conditions found preferable by J. Ewers, et al in the paper cited previously are as follows:

$H_2O$ concentration in the rearranger: 0.2 wt.%
$H_2SO_4$ concentration in the rearranger: 0.15–0.25 wt.%
Rearrangement temperature: 50°–55° C.
para-diisopropylbenzene dihydroperoxide concentration: 10–11 wt.%
Residence time in rearranger: 5 min.

We prefer a continuous process for the rearrangement of the para-diisopropylbenzene dihydroperoxide wherein the para-diisopropylbenzene dihydroperoxide containing complex mixture at a concentration of from about 12 to about 22% by weight, preferably about 18%, in a mixture of acetone and methyl isobutyl ketone, is mixed with a 50% aqueous solution of hydrogen peroxide in a mole ratio of $H_2O_2$ to p-MOXOL (hydroxyhydroperoxide impurity in the para-diisopropylbenzene dihydroperoxide—containing complex mixture) from about 0.5 to about 1.0, preferably about 0.7, and the mixture added at a rate of from about 60 cc/min to about 100 cc/min, preferably 82 cc/min, into the rearranger while simultaneously adding and continuously mixing therewith a sulfuric acid solution in a suitable water soluble organic solvent at a rate of from about 0.17 to about 0.28 cc/min, preferably about 0.23 cc/min of concentrated sulfuric acid, and maintaining the acidified para-diisopropylbenzene dihydroperoxide mixture at a temperature of from about 80° C. to about 85° C. with an average residence time of 4 to 5 minutes.

Water soluble organic solvents suitable for dilution of the acid catalyst in this invention are preferably ketones such as dimethyl ketone, methyl isobutyl ketone, and the like, and is preferably the same ketone as is present in the para-diisopropylbenzene dihydroperoxide/ketone solution which is being rearranged. Any water soluble organic solvent may be used which is non-reactive with the concentrated sulfuric acid.

The weight ratio of concentrated sulfuric acid to water soluble organic solvent operative in this invention is from about 1:10 to about 5:1.

Separation and recovery of the hydroquinone from the rearrangement product and ketone solvent is accomplished by subsequent neutralization, preferably with ammonia, salt separation, and extraction of hydroquinone into water. No emulsion is formed in the extraction step as a result of the process of this invention.

The following examples illustrate the preferred embodiments of the invention which is limited only by the appended claims.

COMPARATIVE EXAMPLE 1

A 10 weight percent solution of para-diisopropylbenzene dihydroperoxide in a mixture of acetone and methylisobutyl ketone was mixed with a 50% aqueous solution of hydrogen peroxide in a mole ratio of $H_2O_2$ to p-moxol of 0.7 and continuously added to a stirred reactor at the rate of 82 cc/min while simultaneously adding concentrated sulfuric acid at the rate of 0.23 cc/min. The temperature was maintained at 80°-85° C. and the residence time in the reactor was 4.5 minutes. After allowing sufficient time for the rearranger to line out, a sample was collected and neutralized with ammonia to a pH of 3.6. The sulfate salts were removed with 25 cc. of water. Thereafter an aliquot of the sample was combined with an equal volume of deionized water, shaken for about 15 seconds, and allowed to phase separate.

The time required for complete phase separation was recorded. The sample was shaken and allowed to phase separate at least three times. The average time for phase separation was 30 minutes. Workup of a sample through a solvent stripping tower and phase separator yielded a stable emulsion which prevented clean separation of hydroquinone from the by-product tars.

EXAMPLE 1

The process of Comparative Example 1 was repeated with the concentrated sulfuric acid diluted with dimethyl ketone in a weight ratio of 1:10 respectively. The time for phase separation was about 10 seconds. Subsequent workup through the solvent stripping tower and phase separator yielded no emulsion.

EXAMPLE 2

The process of Example 1 was repeated except that the acid used was undiluted methane sulfonic acid as the rearrangement catalyst. Results similar to those observed in Example 1 were obtained.

The foregoing disclosure and description of the invention is illustrated and explanatory thereof, and various changes in the method steps may be made within the scope of the appended claims without departing from the spirit of the invention.

We claim:

1. In a process for the acid-catalyzed rearrangement of p-diisopropylbenzene dihydroperoxide to the corresponding dihydric phenol, the improvement comprising introducing into a rearranger, at a rate of from about 60 cc/min to about 100 cc/min, a mixture containing a ketone and from about 12 to about 22% by weight of said p-diisopropylbenzene dihydroperoxide, simultaneously adding, at a rate of from about 0.17 cc/min to about 0.28 cc/min, and continuously mixing with said mixture a solution of an acid catalyst dissolved in a water soluble ketone which is non-reactive with the acid catalyst, the weight ratio of acid to water soluble ketone being from about 1 to 10 to about 5 to 1, and maintaining the mixture of said dihydroperoxide, said acid catalyst and said water soluble ketone at a temperature of from about 80° to 85° with an average resident time of four to five minutes in said rearranger.

2. The process of claim 1 wherein the dihydroperoxide is present as a solution in a ketone and wherein the water soluble organic solvent is the same ketone.

3. The process of claim 1 or 2 wherein the ketone is selected from the group consisting of dimethyl ketone, methyl isobutyl ketone, and mixtures thereof.

4. The process of claim 1 wherein said acid comprises undiluted methane sulfonic acid.

5. In a process for the acid-catalyzed rearrangement of p-diisopropylbenzene dihydroperoxide to the corresponing dihydric phenol, the method of eliminating the formation of an emulsion upon subsequent separation and recovery of the dihydric phenol utilizing water comprising introducing, at a rate of from about 60 cc/min to about 100 cc/min, into a rearranger a mixture containing a ketone and from about 12 to about 22% by weight of said p-diisopropylbenzene dihydroperoxide, simultaneously adding, at a rate of from about 0.17 cc/min to about 0.28 cc/min, and continusouly mixing with said mixture a solution of an acid catalyst dissolved in a water soluble ketone which is nonreactive with the acid catalyst, the weight ratio of acid to water soluble ketone being from about 1 to 10 to about 5 to 1, and maintaining the mixture of said dihydroperoxide, said acid catalyst and said water soluble ketone at a temperature of from about 80° to 85° with an average resident time of four to five minutes in said rearranger.

6. The process of claim 5 wherein the ketone is selected from the group consisting of dimethyl ketone, methyl isobutyl ketone, and mixtures thereof.

7. The process of claim 5 wherein the dihydroperoxide is present as a solution in a ketone and wherein the water soluble organic solvent is the same ketone.

* * * * *